United States Patent
Broyer

Patent Number: 5,294,395
Date of Patent: Mar. 15, 1994

[54] THERMAL TREATMENT OF THERAPLASTIC FILAMENTS FOR THE PREPARATION OF SURGICAL SUTURES

[75] Inventor: Ephraim Broyer, Murray Hill, N.J.

[73] Assignee: Ethicon, Inc., Somerville, N.J.

[21] Appl. No.: 60,881

[22] Filed: May 12, 1993

Related U.S. Application Data

[63] Continuation of Ser. No. 690,140, Apr. 23, 1991, abandoned, which is a continuation-in-part of Ser. No. 402,092, Sep. 1, 1989, abandoned.

[51] Int. Cl.$^5$ .................. D01D 5/08; D01D 10/02
[52] U.S. Cl. ................. 264/178 F; 264/210.5; 264/210.7; 264/210.8; 264/211.15; 264/211.17; 264/235; 264/342 RE
[58] Field of Search ............ 264/178 F, 181, 210.5, 264/210.7, 210.8, 211.14, 211.15, 211.17, 235, 342 RE

[56] References Cited

U.S. PATENT DOCUMENTS

| | | | |
|---|---|---|---|
| 2,346,208 | 4/1944 | Conaway et al. | 8/132 |
| 3,217,074 | 11/1965 | Gould et al. | 264/210 |
| 3,343,363 | 9/1967 | Stow et al. | 57/140 |
| 3,630,205 | 12/1971 | Listner | 128/335.5 |
| 3,776,997 | 12/1973 | Jung et al. | 264/290 |
| 3,957,936 | 5/1976 | Lauchenauer | 264/53 |
| 4,009,511 | 3/1977 | Gauntt | 264/178 F |
| 4,052,988 | 1/1976 | Doddi et al. | |
| 4,246,904 | 1/1981 | Kaplan | 128/335.5 |
| 4,621,638 | 11/1985 | Silvestrini | 264/178 F |
| 4,629,654 | 4/1985 | Sasaki et al. | |
| 4,911,165 | 12/1988 | Lennard et al. | |
| 4,921,668 | 5/1990 | Anderson et al. | 264/80 |
| 5,082,610 | 1/1992 | Fish, Jr. et al. | 264/210.8 |
| 5,102,419 | 4/1992 | Gertzman et al. | 264/210.8 |

FOREIGN PATENT DOCUMENTS 1588031 4/1981 United Kingdom.

OTHER PUBLICATIONS

Vol. 10, No. 355 (C-388) 2411, Nov. 29, 1986, "Production of Improved Polypropylene Monofilament".

Primary Examiner—Leo B. Tentoni
Attorney, Agent, or Firm—Hal Brent Woodrow

[57] ABSTRACT

Thermoplastic monofilament sutures having improved flexibility and handling characteristics are obtained by a melt spinning process which includes the step of drawing the filaments in a heated zone maintained at a temperature above the melting temperature of the filament. The resulting monofilament sutures have a higher elongation and lower modulus than comparable monofilament sutures obtained without the heated drawing step, and are characterized by a crystalline structure which is more highly ordered in the core of the monofilament suture than in a surrounding annular area.

14 Claims, 3 Drawing Sheets

THERMAL TREATMENT OF THERAPLASTIC FILAMENTS FOR THE PREPARATION OF SURGICAL SUTURES

This application is a continuation of application Ser. No. 690,140, filed Apr. 3, 1992, which is a continuation-in-part of U.S. Ser. No. 402,092 entitled "Thermal Treatment of Thermoplastic Filaments", filed Sep. 1, 1989, now abandoned.

FIELD OF INVENTION

The present invention relates to the production of thermoplastic filaments by extrusion and drawing for the preparation of surgical monofilament sutures, and more particularly, to a process for improving the physical properties of such thermoplastic monofilament sutures by thermal treatment. This invention also relates to surgical monofilament sutures produced by the disclosed process.

BACKGROUND OF THE INVENTION

Monofilaments are prepared from many different thermoplastic polymers for a variety of industrial and professional applications. The physical properties of such monofilaments, such as tensile strength, elongation and modulus, depend on the particular polymer composition and on the method of manufacture. It is known, for example, that melt spun nylon and polyethylene terephthalate polymers produce monofilaments of higher tenacity than, for example, the polyolefins, and that the tenacity of such monofilaments is increased while elongation is decreased by drawing the filaments under conditions to increase molecular orientation.

The use of thermoplastic monofilaments as surgical sutures is well established. Monofilament sutures formed of isotactic polypropylene are described in U.S. Pat. No. 3,630,205, and monofilament sutures of polydioxanone are described in U.S. Pat. No. 4,052,988.

Copolymers of p-dioxanone and glycolide useful in preparing monofilament sutures are described in U.S. Pat. No. 4,635,497, while sutures comprising poly [tetramethylene terephthalate-co-(alkenyl or alkyl) succinate] are described in U.S. Pat. No. 4,388,426. Other polymers suggested for use as synthetic absorbable sutures are disclosed in the literature and are well-known to those skilled in the art.

It is generally desirable for surgical sutures to Posses high tenacity (greater than 50,000 psi), low to moderate elongation (from 20–60%), and low modulus (less than 500,000 psi). Low modulus values signify a high degree of filament flexibility and limpness as opposed to a stiff, wiry material, a particularly desirable and even essential feature of a surgical suture. U.S. Pat. No. 3,630,205 describes a process whereby the flexibility of polypropylene sutures may be improved with little sacrifice in tensile strength by stretching the monofilament about 6.6× under controlled conditions and then relaxing to 76–91% of the stretched length.

U.S. Pat. No. 4,246,904 describes a surgical suture prepared from a segmented polyether-ester block copolymer which is reported to have excellent strength and flexibility compared to prior art monofilament sutures. The sutures of poly(p-dioxane) described in U.S. Pat. No. 4,052,988 are also characterized as possessing good tensile and knot strength and a high level of flexibility and softness.

The desirability of suture flexibility and softness as indicated by low modulus values is well recognized by the surgical profession and is a physical property constantly sought after in connection with the development of new surgical suture products. Some suture materials, such polylactide, polyglycolide, and copolymers of lactide and glycolide are generally considered to be too stiff and wiry to be used as monofilaments in all but the smallest suture sizes, and have found commercial acceptance in the larger sizes only as braided sutures, which are more flexible by virtue of their physical construction.

It is accordingly an object of the present invention to provide a process whereby monofilament sutures having improved softness and flexibility may be prepared. It is a further object of this invention to provide a process for reducing the modulus of existing monofilament suture materials with little or no loss of tensile strength. It is yet a further object of this invention to provide improved surgical monofilament sutures of poly(p-dioxanone) and other suitable polymeric materials characterized by reduced values of Young's modulus. A further object of this invention is to provide a method whereby the surface characteristics of thermoplastic suture monofilaments may be modified to enhance the properties of such suture monofilaments, particularly surface smoothness and integrity. These and other objects will be apparent from the ensuing description and claims.

SUMMARY OF THE INVENTION

In the basic embodiment of the present invention, drawn and oriented thermoplastic suture monofilaments are subjected to a heat treatment to reduce modulus and otherwise improve physical properties by passing the suture filament through a radiant heater maintained above the melting temperature of the suture monofilament. Operating conditions are controlled so that the suture monofilament is subjected to a sufficient time/temperature exposure to modify the near-surface crystalline structure of the suture monofilament.

The suture monofilament is maintained under tension and preferably drawn slightly during the heat treatment. Draw ratios of 10–20 percent or higher are possible with most materials. Treatment temperature may be 5° to 100° C. or more above the melting temperature of the suture monofilament, with exposure time adjusted to obtain the desired effect on crystalline structure without penetrating too deeply within the suture monofilament. Following the heat treatment, the monofilament is relaxed and annealed to further increase crystallinity and decrease the degree of amorphous orientation, and then sterilized to render the monofilament suitable for use as a surgical suture.

In a further embodiment of the present invention, melt extruded, liquid quenched suture monofilaments are drawn through a radiant heater maintained at a temperature above the melting temperature of the suture monofilaments. Draw speed, draw ratio, heater temperature and dwell time are regulated to obtain the maximum stable draw ratio for the particular suture monofilament material. This draw ratio will generally be 3× to 6× and 10 to 30 percent more than the maximum stable draw ratio obtainable in the absence of the radient heater. The use of the radiant heater to increase the overall stretch imparted to the suture filament during the initial drawing and orientation step further improves the ultimate physical properties obtainable by the method of this invention. The suture filaments thus produced are further processed according to the basic embodiment of the invention.

Monofilaments, drawn and heat treated in accordance with the present invention, are further processed through relaxation and annealing, as well as sterilization, following conventional procedures. The resulting monofilament sutures are found to have significantly greater elongation, significantly lower modulus and substantially equivalent tensile strength as compared to monofilament sutures processed without the heat treating step of the present invention.

DETAILED DESCRIPTION OF INVENTION

In one embodiment of the present invention, there is provided a process for drawing and relaxing prepared suture filaments in order to modify and improve the properties of such monofilament sutures. The suture filaments subjected to such process have already been prepared by conventional methods of melt extruding, quenching, drawing, and relaxing continuous thermoplastic monofilaments. This embodiment of the invention is referred to herein as the "redraw process".

In a second embodiment of the present invention, there is provided an improved process for the initial preparation of the suture filaments which are to be further processed by the redraw process. This embodiment of the invention, hereinafter referred to as the "extrusion process", in combination with the redraw process, constitutes a preferred embodiment of total invention and results in monofilament sutures having optimum properties.

Figure 1:
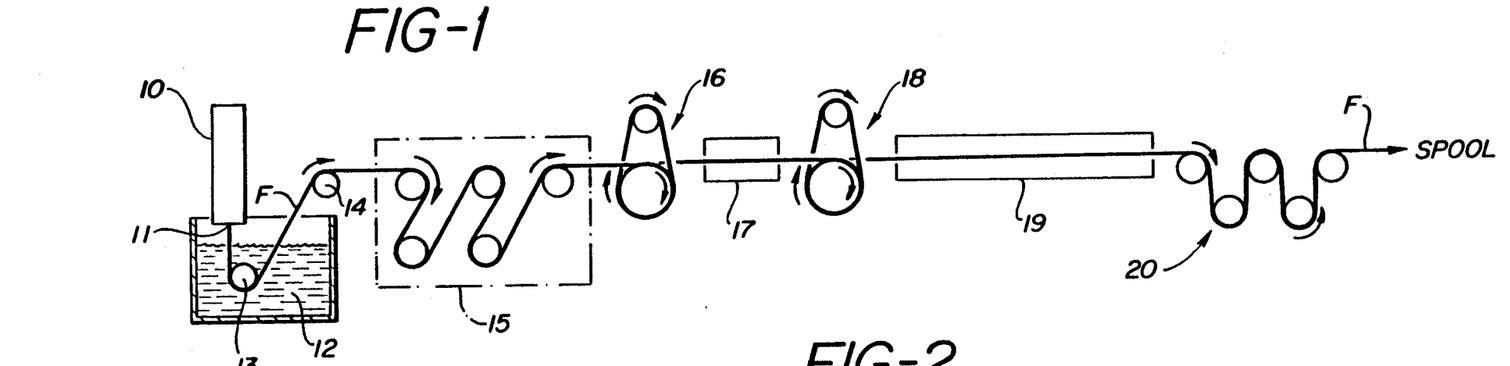
FIG. 1 is a schematic representation of a filament extrusion process for the preparation of a surgical suture according to the present invention.

The extrusion process of the present invention is first described as follows with reference to FIG. 1. The selected thermoplastic polymer is melt extruded using conventional melt spinning apparatus indicated generally as 10. The polymer passes from the spinnette 11 having one or more jet orifices sized to provide the correct final diameter of the desired monofilament into aqueous quench bath 12 where the molten polymer stream hardens into filament F. The filament passes around submerged roll 13 and exits the quench bath over roll 14, thereafter passing into air cabinet 15 where the filament is dried and conditioned before entering the drawing portion of the process. The roll speed in cabinet 15 may be adjusted to take up the filament at a rate faster then the filament is being extruded from the orifice in which case the rolls impart a "jet-stretch" to the filament. The amount of jet stretch, together with orifice size, is adjusted to produce a monofilament of the desired diameter.

The filaments pass from air cabinet 15 to draw rolls 16 which are generally maintained at the same peripheral speed as the rolls in the cabinet so the filaments are maintained under tension but not significantly drawn at this point. The filaments leaving draw rolls 16 pass through tube furnace 17 onto draw rolls 18 which operate at a higher peripheral speed than draw rolls 16 in order to impart a high degree of stretch to the filaments, i.e., 3×–6× (200–500%). The tube furnace, which is optional at this point in the present invention, is operated at a temperature of from 5 to 100° above the melting temperature of the filaments, and most generally, from 20 to 75° above the melting point. Because the furnace is relatively short and the time of filament exposure is short, only the surface of the filament is affected by the heat. The use of the tube furnace at this point in the process allows a higher degree of stretch to be imparted to the filament, but for some polymer systems, the furnace may be omitted and the filament given a cold, warm air or hot water stretch. In any case, the drawing at this stage imparts molecular orientation to the filaments which are essentially amorphous or unoriented spherolitic structures going onto rolls 16. After drawing, the filaments pass through hot air orientation oven 19, maintained at a temperature between the Tg and the melting point of the polymer, where they are given a small additional stretch of e.g. 10–25% by draw rolls 20. This completes the initial filament preparation stage of the process and the filaments are spooled and stored for further processing in the redraw process of the present invention.

Figure 2:
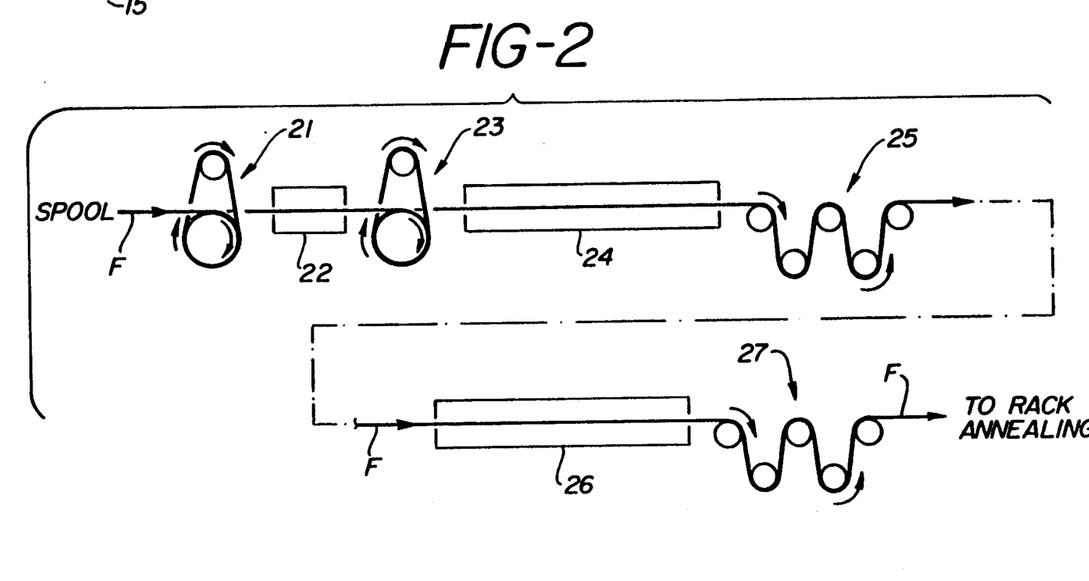
FIG. 2 is a schematic representation of a filament redraw process for the preparation of a surgical suture according to the present invention.

The redraw process is next described with reference to FIG. 2 as follows. Filaments F prepared and spooled in the extrusion process or obtained from other suitable source are fed to draw roll 21, through tube furnace 22, and onto draw rolls 23. The filament is drawn usually less than 100% and most generally from 10 to 25% between rolls 21 and 23. The tube furnace, which is an essential component of the redraw process, is operated at a temperature at least 5° C. above the melting point of the filaments, and preferably at least 15° or more above the melting point. In general, the maximum temperature which is consistent with good operation is preferred and the optimum temperature for any given process will be dependent on filament size and composition, operating speed, and draw ratios. Such optimum temperatures are readily determined by experimental procedures for any given system.

The drawn and heat treated filament proceeds from rolls 23 through hot air conditioning oven 24 and on to draw rolls 25 which operate at a peripheral speed slightly above that of rolls 23, e.g. 2–10%, in order to maintain the filaments under tension. The filaments next proceed from rolls 25 through hot air relaxing oven 26 and onto rolls 27. Rolls 27 operate at a peripheral speed which is 10 to 30% slower than that of rolls 25 in order to permit the filaments to shrink a controlled amount while passing through oven 26. The temperatures in oven 24 and oven 26 are maintained above the Tg but below the melting temperature of the filament, usually about 5 to 20° C. below the melting point.

Filaments leaving rolls 27 are collected and optionally subjected to further processing if desired, to enhance physical properties of the filaments such as annealing to increase crystallinity. After these additional optional steps, the filaments are sterilized so the filaments are suitable for use as a surgical suture. Sterilization can be carried out, for example, by subjecting the filaments to cobalt 60 radiation or ethylene oxide vapor. Other sterilization means can be used if desired.

The tube furnace, which is an essential component of the redraw process, and an optionally preferred component of the extrusion process, is preferably a high temperature furnace which heats by radiant energy as well as convection. A suitable furnace for single or small groups of monofilaments is tube furnace Model No. 55035 available from the Lindberg Co., 304 Mart Street, Watertown, Wis. This furnace is designed to reach temperatures of up to 900° C., and is heated by electrical elements backed by a refractory material. The furnace has a 1-inch diameter tubular opening through which the filaments pass. It is important when using this furnace that the filaments be centered in the opening to avoid uneven heating. For larger scale multifilament suture production, a furnace with infrared heaters and parallel heating plate geometry would be preferred to a tubular furnace.

The method of the present invention is illustrated by the following example describing the preparation of a monofilament suture of poly(p-dioxanone). Poly(p-dioxanone) sutures are known from U.S. Pat. No. 4,052,988, incorporated herein by reference. The preparation of p-dioxanone monomer and polymerization of that monomer to obtain polymers having intrinsic viscosities in excess of 0.80 are described in this reference. Further, the extrusion of the polymer according to Example VI of this reference resulted in monofilaments having a diameter of 11 mils (corresponding to a 3/0 suture) a tensile strength of 55,600 psi, a dry knot strength of 48,800 psi, and a Young's modulus of 167,000 psi. Example VII describes a 9 mil monofilament having a tensile strength of 70,600 psi, dry knot strength of 50,300 psi, and an elongation of 46.3 percent.

A commercial monofilament suture comprising a polymer of p-dioxanone and manufactured and sold by Ethicon, Inc., Somerville, N.J. under the trademark "PDS ® Suture", has been determined to have average properties as shown in Table I below.

Poly(p-dioxanone) sutures size 2/0 and 5/0 were produced from the same polymer as aforedescribed commercial sutures by the method of the present invention. The physical properties of these sutures are also presented in Table I below. As illustrated by these data, the sutures produced according to the present invention have similar tensile and knot strength, greater elongation, and significantly lower modulus than the commercial sutures.

TABLE I

| | Suture Properties | | | |
|---|---|---|---|---|
| | This Invention | | Commercial Product | |
| Suture Size | 5/0 | 2/0 | 5/0 | 2/0 |
| Diameter (mil) | 6.8 | 13.5 | 6.5 | 13.7 |
| Tensile (lb) | 3.4 | 12.6 | 2.9 | 11.1 |
| Intr. ten. (psi) | 92,770 | 88,775 | 87,550 | 75,010 |
| Elong. (%) | 58.0 | 60.0 | 38.1 | 34.1 |
| Knot (lb) | 2.3 | 7.3 | 2.1 | 7.0 |
| Intr. knot (psi) | 63,130 | 51,280 | 62,000 | 47,140 |
| Modulus (psi) | approx. 200,000 | | approx. 330,000 | |

The reduced modulus and increased elongation of the sutures of the present invention impart improved handling characteristics and reduced tissue drag which are readily perceived and preferred by surgeons using these materials. In particular, the reduced modulus results in greater flexibility and less springiness than that characteristic of the commercial product. The poly(p-dioxanone) sutures of the present invention were found to have essentially the same in vivo breaking strength retention and absorption characteristics as the commercial product.

The sutures of the present invention reported in Table I were prepared by the process as generally described below. This process is described specifically for the manufacture of poly(p-dioxanone) sutures wherein the starting polymer has an average molecular weight of from about 65,000 to 100,000, an inherent viscosity of from about 1.60 to 2.20, and a melting temperature of from about 95 to 105° C. Process conditions may vary for other polymer compositions including other poly(p-dioxanone) polymers and the following example is accordingly presented for purposes of illustration only as being representative for one specific polymer system and is not otherwise limiting of the present invention. Many variations in the process equipment and operating parameters which nevertheless incorporate the essential features of the present invention will be apparent to those skilled in the art and are intended to be included within the scope of the present invention.

EXAMPLE (size 2/0)

Poly(p-dioxanone) polymer having an average MW of about 78,000, an inherent viscosity of 1.65–1.80 (melting point approx. 95° C.) was melt extruded through a 60 mil orifice and quenched in a water bath at 24° C. The extruded filament was conditioned to about 80° C. in a warm air cabinet and fed to a draw station where it was drawn 5× between two set of godets while passing through a tube furnace at 125° C. The first godet speed was 13 FPM, the second godet speed was 65 FPM, and the furnace was 12 inches long. Filament dwell time in the furnace was estimated to be about 1 second. The drawn filament was drawn an additional 20% while passing through a hot air oven maintained at about 80° C. The filament was collected and conditioned under vacuum at room temperature for 16 hours. The monofilament was next drawn 15% while passing through a 12 inch tube furnace maintained at about 115-120° C. Dwell time in the furnace was estimated to be approximately 1.5 seconds. The drawn filament was next passed through a hot air oven maintained at about 90° C. with a 4% stretch to maintain tension, followed by a second oven at 90° C. wherein the filament was allowed to shrink 15%. The resulting filament was wound on a rack for annealing at a temperature of from about 70 to 90° C., and, in the present example, at 85° C. for 6 hours while maintained under tension to prevent further shrinkage. The resulting monofilament had a diameter of 14 mils corresponding to a size 2/0 surgical suture.

The above procedure was repeated to prepare sutures ranging in size from 7/0 (0.4 mils) to 2 (23 mils). Individual suture sizes were obtained by adjusting extrusion rates and/or orifice size to produce an extruded monofilament which, after passing through the remainder of the process which resulted in a 6× overall stretch, would produce the desired suture diameter. While minor adjustments in process speeds and temperatures were made to accommodate the different filament sizes and to optimize process conditions for each size, the basic process was the same as that described above for the size 2/0 suture.

Representative physical properties for sutures prepared in accordance with the present invention as described above are presented in Table II together with comparable data for commercial sutures of the same polymeric compositions. As noted above, the commercial sutures were prepared by a conventional process which did not include heat treatment at a temperature above the melting point of the polymer.

TABLE II

Physical Properties of Sutures of Poly(p-dioxanone)

| Suture Size | This Invention | | | | Commercial Product | | | |
|---|---|---|---|---|---|---|---|---|
| | Straight Tensile (lbs) | Knot Strength (lbs) | Elong. (%) | Strain Load | Straight Tensile (lbs) | Knot Strength (lbs) | Elong (%) | Strain Load |
| 2 | 28.1 | 16.4 | 59.4 | 2.7 | 29.9 | 16.1 | 37.1 | 3.9 |
| 1 | 22.8 | 12.9 | 54.7 | 2.2 | 24.5 | 13.2 | 27.1 | 3.1 |
| 0 | 17.8 | 10.3 | 58.3 | 1.6 | 17.6 | 10.5 | 36.9 | 2.4 |
| 2/0 | 11.0 | 7.2 | 52.0 | 1.0 | 10.9 | 6.8 | 32.3 | 1.8 |
| 3/0 | 7.7 | 5.5 | 51.6 | 0.8 | 8.1 | 5.2 | 34.5 | 1.2 |
| 4/0 | 4.6 | 3.3 | 53.7 | 0.4 | 4.8 | 3.2 | 32.1 | 0.7 |
| 5/0 | 2.9 | 2.2 | 44.6 | 0.3 | 3.0 | 2.1 | 33.3 | 0.4 |
| 6/0 | 1.3 | 1.0 | 50.6 | 0.1 | 1.3 | 0.9 | 29.1 | 0.2 |
| 7/0 | 0.8 | 0.7 | 52.6 | 0.1 | 0.6 | 0.6 | 26.1 | 0.1 |

As illustrated by the data in Table II, which are generally representative of these products, sutures prepared according to the present invention are substantially equivalent to the commercial sutures in straight tensile and knot strength, but have significantly higher elongation. In addition, the sutures of the present invention possess a higher degree of elasticity as indicated by the Strain Load which is a measure of the force required to reach the 3% strain level in a stress-strain test. The lower the strain load value, the more stretchy the suture is perceived to be.

Sutures of poly(p-dioxanone) were also evaluated for tensile strength, modulus, and Gurley Stiffness with the representative results presented in Table III below.

to the present invention are specifically characterized by the following physical properties:
Elongation—greater than 40%
Young's Modulus—less than 250,000 psi
Tenacity/Modulus ratio—greater than 0.30

Test methods used for determining the physical properties of monofilament suture materials were as follows:

Tensile strength, knot strength and percent elongation at break were determined by A.S.T.M. method D-2256-66T at a constant rate of extension using an INSTRON table Model 4200 universal testing instrument manufactured by the Instron Corporation of Canton, Mass. With the instrument sample clamps set 5 inches apart, 5-inch lengths of suture were elongated at a rate of 12 inches per minute until fracture. The suture knot strength was determined under the same test conditions.

The INSTRON instrument was set for the correct suture diameter, and Young's Modulus was calculated in psi from the initial stress-strain data generated during the straight tensile strength test. Young's Modulus is the ratio of applied stress to

TABLE III

Physical Properties of Sutures of Poly(p-dioxanone)

| Nominal Suture Size | This Invention | | | | | Commercial Product | | | | |
|---|---|---|---|---|---|---|---|---|---|---|
| | Diameter mils | Gurley Stiffness | Ten. (psi × $10^{-3}$) | Mod. | Ten./Mod. | Diameter mils | Gurley Stiffness | Ten. (psi × $10^{-3}$) | Mod. | Ten./Mod. |
| 2 | 23.3 | 240 | 63.7 | 210 | 0.30 | 23.8 | 364 | 72.5 | 336 | 0.22 |
| 1 | 20.8 | 149 | — | — | — | 19.6 | 169 | 75.7 | 318 | 0.24 |
| 0 | 18.4 | 85 | 69.1 | 200 | 0.35 | 17.0 | 118 | 71.8 | 323 | 0.22 |
| 2/0 | 14.1 | 30 | 70.2 | 198 | 0.35 | 13.6 | 54 | 73.4 | 337 | 0.21 |
| 3/0 | 12.0 | 16 | 74.2 | 204 | 0.36 | 11.6 | 23 | 75.3 | 333 | 0.23 |
| 4/0 | 8.4 | 5.6 | — | — | — | 8.7 | 7.0 | 82.3 | 354 | 0.23 |
| 5/0 | 6.6 | 1.8 | 82.6 | 199 | 0.43 | 6.9 | 2.6 | 77.2 | 334 | 0.23 |
| 6/0 | 4.4 | 0.2 | — | — | — | 4.4 | 0.2 | 89.6 | 322 | 0.28 |
| 7/0 | 0.4 | 0.04 | — | — | — | 0.4 | 0.04 | — | 351 | — |

As shown by the above data, the sutures prepared according to the present invention have significantly lower modulus than the commercial product, approximately 200,000 psi vs. 330,000 psi. This lower modulus is also reflected in the Gurley Stiffness values which are significantly lower for the sutures of the present invention compared to the commercial product. In this particular study, the tensile strength of the test sutures was slightly lower than that of the commercial product. Further process refinement and optimization of operating conditions however, would be expected to produce further improvement of the physical properties of sutures prepared according to the present invention, including increased tensile strength. Particularly preferred sutures of poly(p-dioxanone) prepared according strain in the elastic region of the suture and measures the elastic component of a suture's resistance to stress. This value is related to the flexibility of a suture.

Gurley stiffness was measured using a motor-operated Gurley Stiffness Tester (Model 4171-D) manufactured by Teledyne-Gurley of Troy, N.Y. In the test, 10 parallel monofilaments are mounted on a fixture so that the filaments extend precisely ⅜ inch beyond the edge of the fixture. The instrument is adjusted to provide ¼ inch clearance between the edge of the fixture and the pendulum so that the pendulum acts against ¼ inch of the monofilaments. The instrument is operated and filament stiffness computed according to the manufacturer's instructions.

Good suture flexibility as indicated by low Gurley Stiffness values is important to the surgeon since soft, highly flexible sutures are easier to handle, use and tie. Flexible and slightly elastic sutures are also desirable since they conform to the wound and permit some latitude in the tension applied to the suture by the surgeon.

In addition to their desirable physical properties, monofilament sutures produced according to the present invention are characterized by a unique morphology which includes a central core having a highly ordered crystalline structure and an annular portion between the central core and outer surface which has a less ordered crystalline structure. This differentiation in crystalline structure is believed to be the result of exposing the suture filament to high temperatures in excess of the melting point of the polymer for brief periods during the manufacturing process as described above. While applicant does not wish to be bound by theory, it is postulated that the surface of the suture filament may actually melt as the filament passes through the heater section, and the penetration of heat into the body of the filament results in the difference in crystalline structure noted above. The thickness of the annular portion which may be from about 0.1 to 0.5× the radius of the suture filament is a measure the degree of heat penetration which is a function of the time and temperature of exposure.

Figure 3:
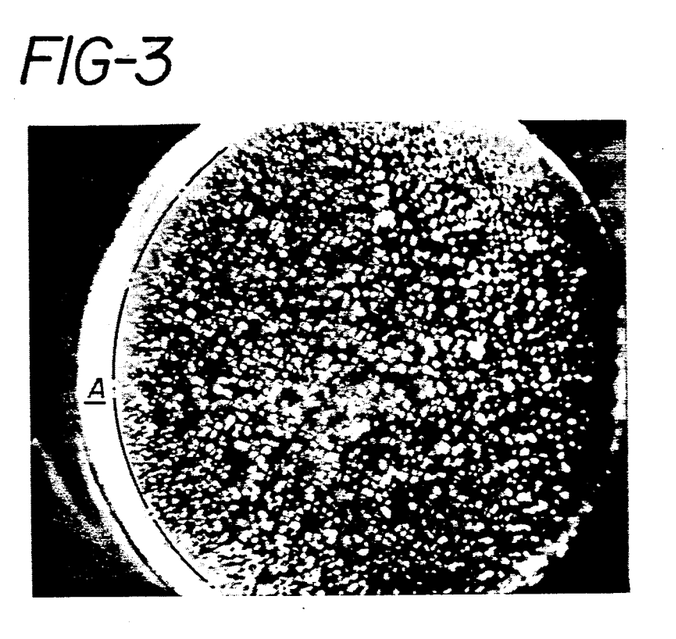
FIG. 3 is a cross-section photomicrograph of a size 4/0 monofilament suture of poly(p-dioxanone) prepared according to the method of the present invention.
Figure 4:
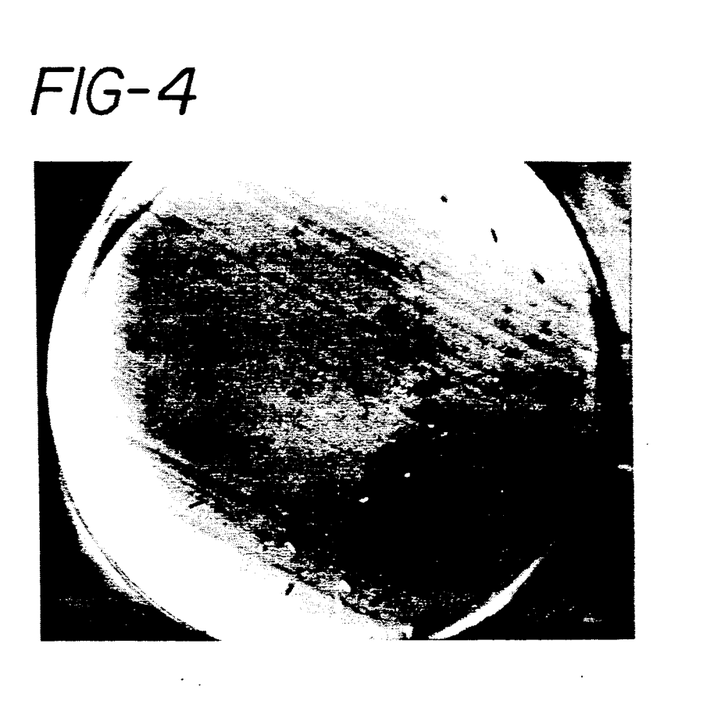
FIG. 4 is a cross-section photomicrograph of a size 4/0 monofilament suture of poly(p-dioxanone) prepared according to the prior art.
Figure 5:
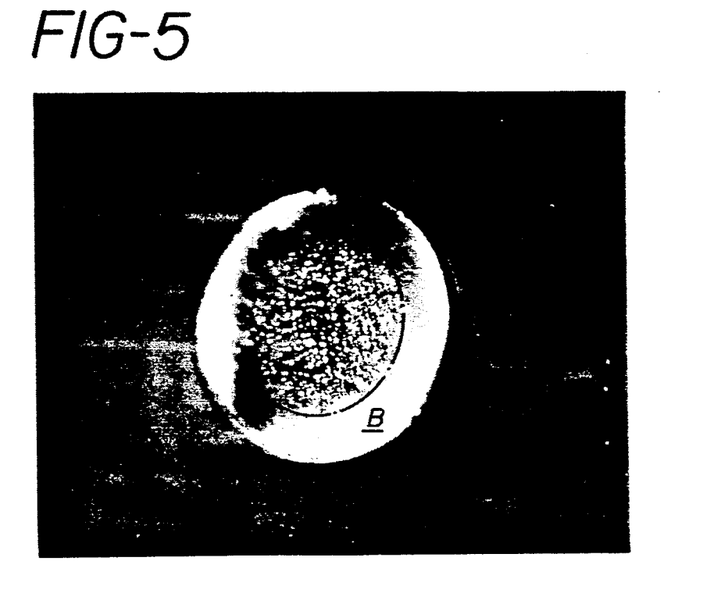
FIG. 5 is a cross-section photomicrograph of a size 6/0 monofilament suture of poly(p-dioxanone) prepared according to the method of the present invention.
Figure 6:
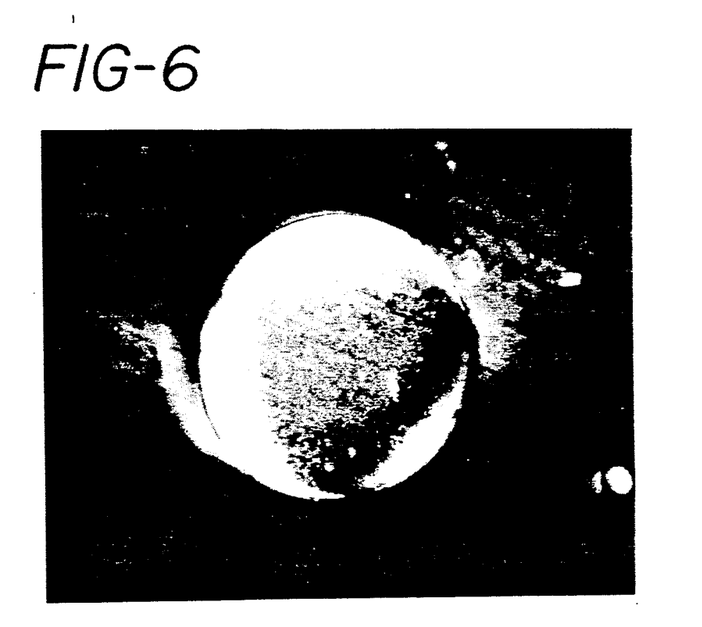
FIG. 6 is a cross-section photomicrograph of a size 6/0 monofilament suture of poly(p-dioxanone) prepared according to the prior art.

The morphological differences between the poly(p-dioxanone) monofilament sutures produced according to the present invention and the commercial sutures of the same polymeric composition are readily apparent in FIG. 3 and FIG. 4, which are 430× photomicrographs of cross-sections of size 4/0 filaments illuminated with polarized light. The commercial product illustrated in FIG. 4 is seen to have a relatively uniform crystalline structure throughout its cross-section. The monofilament suture of the present invention illustrated in FIG. 3 is seen to have a clearly defined central core surrounded by annular area A which extends inward from the surface of the filament a distance equal to about 0.2× the radius of the suture. The crystalline structure of the central core appears to be highly ordered and characterized by large, possibly spherolitic crystals. The annular area surrounding the core appears to have appreciably smaller crystals indicative of a less ordered structure. This observed difference in crystalline structure is theoretically consistent with the effect of the different processing conditions used in the manufacture of the two products. The same effect is seen in FIG. 5 and FIG. 6 which are respectively 430× photomicrographs of size 6/0 sutures of the present invention and commercial product. In FIG. 5, annular area B extends inward from the surface of the suture a distance equal to about 0.4× the radius of the suture.

The differences in crystalline structure between the poly(p-dioxanone) sutures of the present invention and the commercial product are readily determined by x-ray diffraction patterns and scattering analysis as illustrated by the representative values shown in Table IV.

TABLE IV

| | Crystalline Properties of Poly(p-dioxanone) Sutures | | | | | | | |
|---|---|---|---|---|---|---|---|---|
| | This Invention | | | | Commercial Product | | | |
| Suture Size | $X_c$ | L | $l_s$ | $F_h$ | $X_c$ | L | $l_s$ | $F_h$ |
| 2/0 | 0.52 | 78 | 95 | 206 | 0.47 | 64 | 96 | 229 |
| 4/0 | 0.55 | 72 | 97 | 208 | 0.52 | 61 | 97 | 245 |
| 6/0 | 0.56 | 76 | 97 | 180 | 0.51 | 71 | 99 | 213 | where:
$X_c$ is the relative crystallinity calculated as $$X_c = \Sigma I_c / \Sigma I_t$$

where $\Sigma I_c$ is the integrated area under the crystalline peaks, and $\Sigma I_t$ is the integrated area under the observed diffraction curve.

L is an estimate of the breadth in Å of individual crystallites using the Debye-Scherrer equation $$L = \lambda / \beta \cos \theta$$

where $\theta$ is half the diffraction angle, $\lambda$ is the wave length of radiation in Å, and $\beta$ is the peak width in Å at half-height.

$l_s$ is a measure of the long range crystalline structure determined by small angle radiation scatter as the average distance in Å from the center of one crystallite to the center of the next measured in the chain direction along the fiber axis.

$F_h$ is a measure of the long range crystallite perfection in the chain direction along the fiber axis as indicated by crystalline peak width in Å at half-height using the Debye-Scherrer equation as defined above.

The method of the present invention has been illustrated with specific reference to monofilament sutures of Poly(p-dioxanone) having unique morphology and improved physical properties, and such sutures are part of the present invention. The method of the present invention however, has wide application for the preparation of monofilament sutures used with other thermoplastic polymeric compositions. Such polymeric compositions which are contemplated for use in the method of the present invention include polyethylene, polypropylene, polyvinylidene fluoride, poly(glycolide, co-trimethyl carbonate), homopolymers and copolymers of lactide and glycolide and copolymers of p-dioxanone with lactide, glycolide and ε-caprolactone.

Many variations in the details of the process of the present invention will be apparent to those skilled in the art and may be made without departing from the spirit and scope thereof. The process may, for example, incorporate further drawing, relaxing and annealing stages in addition to those disclosed herein or may omit or modify one or more of the nonessential processing steps described herein. In addition, the essential feature of the present invention which involves heat treating a suture monofilament comprising a thermoplastic polymer at a temperature in excess of the melting point of that polymer, is subject to variation according to the composition of the polymer, the size of the monofilament, and the time/temperature relationship of the heat treating step. For example, while the preceeding description included temperatures as high as 75° C. above the melting point of the polymer, and exposure times as brief as 0.1 seconds, it may be desirable for higher production speeds or for other purposes to reduce exposure times to 0.01 seconds or less while increasing the temperature up to several hundred degrees above the melting point of the polymer as necessary to obtain the desired effect on the morphology of the monofilament suture and its physical properties. It is accordingly understood that this invention is not limited to the specifically described embodiments except as may be defined in the claims appended hereto.

I claim:

1. In a method for producing a monofilament suture composed of a thermoplastic polymeric composition, said thermoplastic polymeric composition selected from the group consisting of poly(p-dioxanone), polyethylene, polypropylene, polyvinylidene fluoride, poly(glycolide, cotrimethyl carbonate), homopolymers and copolymers of lactide and glycolide and copolymers of p-dioxanone with lactide, glycolide and ε-caprolactone, comprising the steps of melt extruding and quenching the polymer to form a continuous suture filament, drawing the suture filament to achieve molecular orientation, relaxing or annealing the drawn suture filament to relieve internal stresses, and thereafter sterilizing the filament to render the filament suitable for use as a surgical suture, the improvement comprising exposing the suture filament to a temperature in excess of the melting temperature of the polymeric composition during or subsequent to drawing the said suture filament and prior to the relaxation or annealing of said drawn suture filament, said exposure being for a time and at a temperature effective to obtain a suture filament having a lower order of crystallinity in the outer core area and a higher order of crystallinity in the inner core area.

2. The method of claim 1 wherein said exposure occurs during a first drawing of the extruded and quenched suture filament.

3. The method of claim 1 wherein said exposure occurs after a first drawing of said extruded and quenched suture filament, and said suture filament is maintained under tension during said exposure.

4. The method of claim 1 wherein said suture filament is exposed a first time during a first drawing of said extruded and quenched suture filament, and is exposed a second time during a second drawing of said drawn suture filament.

5. The method of claim 1 wherein a first drawing is in excess of 200 percent and said second drawing is less than 100 percent.

6. The method of claim 1, wherein the outer core area has a radial thickness of from about 0.1 to 0.5× the radius of the suture filament.

7. Method of claim 1 wherein said temperature of exposure is from about 5 to 100° C. above the melting temperature of said polymer.

8. Method of claim 7 wherein the time of said exposure is from about 0.1 to 5 seconds.

9. Method of claim 1 wherein said polymer is poly(p-dioxanone).

10. Method of claim 9 wherein said extruded and quenched suture monofilament is drawn 4 to 6× while being exposed to a temperature of from about 105° C. to 175° C. for a period of from about 0.1 to 5 seconds.

11. Method of claim 10 wherein said suture filament is drawn 5× while being exposed to a temperature of about 120 to 140° C.

12. Method of claim 10 wherein said drawn and exposed suture filament is redrawn about 5 to 30% while being exposed a second time to a temperature of from about 105 to 175° C. for a period of from about 0.1 to 5 seconds.

13. The method of claim 12 wherein said redrawn and exposed suture filament is relaxed by shrinking 10 to 25% of its redrawn length at temperature below its melting point.

14. The method of claim 13 wherein said suture filament is annealed after relaxation at a temperature of from about 70 to 90° C. while being restrained against further shrinkage.

* * * * *

UNITED STATES PATENT AND TRADEMARK OFFICE
CERTIFICATE OF CORRECTION

PATENT NO. : 5,294,395
DATED : March 15, 1994
INVENTOR(S) : Ephraim Broyer

It is certified that error appears in the above-indentified patent and that said Letters Patent is hereby corrected as shown below:

On the title page and in column 1, lines 1-4,
correct the title to read as follows:

Thermal Treatment of Thermoplastic Filaments For The Preparation of Surgical Sutures Signed and Sealed this Fifteenth Day of November, 1994

Attest:

BRUCE LEHMAN

*Attesting Officer*  *Commissioner of Patents and Trademarks*